(12) United States Patent
Weiss et al.

(10) Patent No.: US 8,594,788 B2
(45) Date of Patent: Nov. 26, 2013

(54) CARDIAC STIMULATOR FOR DELIVERY OF CARDIAC CONTRACTILITY MODULATION THERAPY

(75) Inventors: Ingo Weiss, Berlin (DE); Thomas Doerr, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 13/494,984

(22) Filed: Jun. 12, 2012

(65) Prior Publication Data
US 2013/0006318 A1    Jan. 3, 2013

Related U.S. Application Data

(60) Provisional application No. 61/501,766, filed on Jun. 28, 2011.

(51) Int. Cl.
*A61N 1/365* (2006.01)
*A61N 1/36* (2006.01)

(52) U.S. Cl.
USPC .................................................. 607/17; 607/9

(58) Field of Classification Search
USPC ............................................ 607/4, 9, 14, 17
See application file for complete search history.

(56) References Cited

U.S. PATENT DOCUMENTS

| 6,115,633 A * | 9/2000 | Lang et al. ....................... 607/17 |
| 6,317,631 B1 | 11/2001 | Ben-Haim et al. |
| 2003/0028221 A1 | 2/2003 | Zhu et al. |
| 2004/0049235 A1 * | 3/2004 | Deno et al. ........................ 607/9 |
| 2006/0167529 A1 | 7/2006 | Schecter |
| 2010/0049270 A1 | 2/2010 | Pastore et al. |
| 2010/0069977 A1 | 3/2010 | Stahmann |
| 2010/0069980 A1 | 3/2010 | Stahmann |
| 2010/0069984 A1 | 3/2010 | Stahmann |
| 2010/0069985 A1 | 3/2010 | Stahmann |

OTHER PUBLICATIONS

European Search Report, dated Oct. 2, 2012, 5 pages.

* cited by examiner

*Primary Examiner* — Rex R Holmes
(74) *Attorney, Agent, or Firm* — Arc IP Law, PC; Joseph J. Mayo

(57) ABSTRACT

A cardiac stimulator having at least one stimulation unit which is connected or connectable to one or more stimulation electrodes, and is configured to deliver at least sub-threshold stimulation pulses for cardiac contraction modulation therapy, an impedance detection unit which is connectable to one or more electrodes, and is configured to detect a voltage or current intensity that occurs as the result of a particular sub-threshold stimulation pulse, and to determine a particular impedance value, an impedance evaluation unit, configured to determine at least one value based on ventricular volume, and/or a value based on minute ventilation, and a control unit connected to the stimulation unit and the cardiac rhythm detection unit, and is configured to control a delivery of a stimulation pulse via the stimulation unit such that the cardiac stimulator can deliver sub-threshold stimulation pulses for cardiac contraction modulation therapy.

13 Claims, 9 Drawing Sheets

CARDIAC STIMULATOR FOR DELIVERY OF CARDIAC CONTRACTILITY MODULATION THERAPY

This application claims the benefit of U.S. Provisional Patent Application 61/501,766 filed on 28 Jun. 2011, the specification of which is hereby incorporated herein by reference.

BACKGROUND OF THE INVENTION

1. Field of the Invention

At least one embodiment of the invention relates to a cardiac stimulator for the delivery of cardiac therapy.

2. Description of the Related Art

Implantable cardiac stimulators in the form of cardiac pacemakers or cardioverters/defibrillators are typically connected to electrode leads which comprise stimulation electrodes and defibrillation electrodes—the latter of which may be provided in addition thereto, as an option—in a ventricle or in the immediate vicinity. Using a stimulation electrode, a cardiac pacemaker can deliver an electrical stimulation pulse to the muscle tissue of a ventricle to thereby induce a stimulated contraction of the ventricle provided the stimulation pulse has sufficient intensity and the cardiac muscle tissue (myocardium) is not in a refractory phase at the moment. Such a stimulated contraction of a ventricle is referred to as a stimulated event within the scope of this description. If a natural contraction of the ventricle occurs, this is referred to as natural action or a natural or intrinsic event within the scope of this description. A contraction of the right atrium of a heart, for instance, is referred to as an atrial event, which can be a natural atrial event, for instance, or—in the case of an atrial cardiac pacemaker—can also be a stimulated atrial event. In the same sense, a distinction can be made between natural (intrinsic) and stimulated left ventricular events and right ventricular events.

Local excitation of the myocardium propagates from the excitation site by conduction in the myocardium, resulting in depolarization of the muscle cells and thus contraction of the myocardium. After a brief period of time the muscle cells are repolarized and the myocardium therefore relaxes. During the phase of depolarization, the cardiac muscle cells are insensitive to excitation, i.e. they are refractory. This period is referred to as the refractory period. The electrical potentials associated with depolarization and repolarization can be sensed, and the variation thereof over time—referred to as an electrocardiogram—can be evaluated.

The cardiac rhythm of a healthy individual is determined by the sinoatrial node, which is controlled by the autonomic nervous system. It excites—via conduction—the right atrium of a human heart and furthermore, via the AV node, the (right) ventricle of the heart. A natural cardiac rhythm originating in the sinoatrial node is therefore also referred to as sinus rhythm and induces natural contractions of the particular ventricle, which can be detected as natural (intrinsic) events.

Such natural (intrinsic) events are detected by determining the electrical potentials of the myocardium of the particular ventricle using sensing electrodes, which are part of a corresponding electrode lead. The sensing electrodes can also be the stimulation electrodes, and can be used in alternation as stimulation electrodes and as sensing electrodes. Typically, a pair of sensing electrodes composed of two adjacent electrodes, i.e. a tip electrode and a ring electrode, is provided for the sensing, wherein the tip electrode is also used as the stimulation electrode. A bipolar recording of an intracardial electrocardiogram (IEGM) is obtained in this manner. In that case, sensing and stimulation take place in the ventricle using a ventricular electrode lead, and stimulation and sensing take place in the atrium (the right atrium) using an atrial electrode lead which is connected separately to the particular cardiac stimulator. In addition, a left ventricular electrode lead can be provided, which typically extends via the coronary sinus and a lateral vein branching off therefrom into the vicinity of the left ventricle, where it can comprise a stimulation electrode and/or sensing electrode having a small surface area.

During operation of the cardiac stimulator, the sensing electrodes are connected to appropriate sensing units which are designed to evaluate a particular electrocardiogram recorded using a sensing electrode (or a pair of sensing electrodes), and, in particular, to detect intrinsic atrial or ventricular events, i.e. natural atrial or ventricular contractions. This takes place, for example, by comparison with a threshold value, i.e. an intrinsic event is detected when a particular intracardial electrocardiogram exceeds a suitably specified threshold value.

On the basis of the frequency at which the atrial and ventricular events follow one another, the particular intrinsic atrial heart rate (atrial frequency) or ventricular heart rate (ventricular frequency) can be derived, thus enabling detection of tachycardias, for example.

In the case of known demand pacemakers, the detection of natural events is also used to suppress (inhibit) the delivery of stimulation pulses to a particular ventricle if the natural event is detected within a time window before the planned delivery of a stimulation pulse to the ventricle. In the case of rate-adaptive cardiac pacemakers, the point in time for delivery of a particular stimulation pulse is planned depending on a particular stimulation rate, which should correspond to a patient's physiological demand, and is higher when exertion is greater, for instance. For this purpose, a cardiac stimulator can be equipped with one or more activity sensors, which can be a CLS (Closed Loop Stimulation) sensor, for instance, which is described in greater detail below.

The natural effect of the autonomic nervous system on the heart rate, which is simulated by a rate-adaptive cardiac stimulator, is referred to as chronotropism.

Cardiac performance is determined by chronotropism as well as contractility, the influencing of which is referred to as inotropism.

To determine the contractility of a heart, it is known to dispose an impedance or conductivity meter in a housing of a cardiac stimulator (e.g. an implantable cardiac pacemaker), which is designed to generate a unipolar or bipolar signal indicating the variation of impedance or conductivity. For this purpose, a plurality of impedance or conductivity values or a related variation in impedance or conductivity can be measured during at least one cardiac cycle. This takes place either in a unipolar manner by performing a measurement between a neutral electrode and a measuring electrode, or between two measuring electrodes. In addition, an evaluation unit is disposed in the housing, which is used to evaluate the variation in impedance or conductivity, and to determine a contractility value on the basis of the variation in impedance or conductivity. Electrotherapeutic devices that can determine the contractility of a heart can be used to adapt a therapy to be delivered by the electrotherapy device to the particular contractility state of the patient's heart.

As indicated, contractility describes an inotropic state of a heart. Contractility influences the force and speed of a myocardial contraction. Contractility is controlled by three mechanisms:

direct control by the autonomic nervous system (ANS),
    the so-called Starling mechanism, and
    the so-called Bowditch effect (force-frequency coupling).

The main mechanism, the control of circulatory regulation by the autonomic nervous system, increases contractility and heart rate when metabolic demand is elevated e.g. during physical or mental exertion, to ensure suitable blood supply. In a healthy individual, the inotropism of the heart therefore causes contractility to increase due to increased physiological demand.

In patients with chronic heart failure (CHF), myocardial contractility decreases to a low level, and interventricular synchronization is worsened. This is accompanied by a low ejection fraction (EF), and by a low quality of life and high mortality. HF occurs frequently in the population. Recently, HF patients have been treated with resynchronization therapy devices, such as 3-chamber cardiac pacemakers or defibrillators. The objective of such pacemaker therapy is to synchronize the two ventricles of a heart using biventricular stimulation in order to improve the time behavior of the ventricles and, therefore, cardiac performance. Such therapy is also referred to as cardiac resynchronization therapy (CRT). Cardiac resynchronization therapy (CRT) is adequately.

Since the contractility of the heart is controlled physiologically by the autonomic nervous system, the detection of contractility can also be utilized to adjust a physiologically adequate stimulation rate in the case of rate-adaptive cardiac pacemakers. This type of stimulation rate control, which was addressed above, is also known as closed loop stimulation (CLS).

For CLS, the intracardial variation in impedance is measured after the onset of ventricular contraction. The measurement is performed for intrinsic events and stimulated events. There is a direct dependence between the right-ventricular variation in impedance and contraction dynamics. In turn, contraction dynamics are a parameter for stimulation of the heart by the sympathetic nervous system.

As stated, closed loop stimulation is used to control the stimulation rate in the case of a rate-adaptive cardiac pacemaker.

To increase the contractility of a ventricle, it is known to use cardiac contractility modulation (CCM).

Systems for CCM therapy are known from publications such as US 2010/0069977 A1, US 2010/0069980 A1, US 2010/0069984 A1 and US 2010/0069985 A1. A system such these comprises a stimulation pulse generator, connected to 3 electrodes, one of which is disposed in the atrium and two of which are disposed at the septum of the right ventricle of a patient during operation. The therapeutic principle is based on a delivery of biphasic stimulation pulses with an amplitude of 7-10V and a total pulse duration of ~20 ms in the absolute refractory period of the ventricle, with the objective of increasing contractility. The therapy is delivered for certain units of time throughout the day (e.g. 1 h on, 1 h off).

The principle of cardiac contractility modulation therapy is also described, inter alia, in U.S. Pat. No. 6,317,631 B1.

The effect of CCM therapy is based—according to current speculation—on a modification of cellular calcium ion exchange and therefore results in increased contraction force, which should also deliver a therapeutic benefit if atrial fibrillation is present. Although this has not been proven clinically, it can be explained pathophysiologically.

US 2010/0069977 A1, US 2010/0069980 A1, US 2010/0069984 A1, US 2010/0069985 A1 describe various methods for delivering CCM stimulation on demand. Described herein in general is the use of physiological sensors, renal or cardiac function sensors, electrolyte sensors, serum sensors (e.g. creatinine), neurosensors (vagus nerve, sympathetic nervous system), adverse event detectors, worsening heart failure sensors, MRT sensors, activity sensors, sleep apnea sensors, ischemia sensors, sensors for metabolic demand and infarct sensors, and CCM controls that are dependent on cardiac rhythm.

US 2010/0069977 A1, US 2010/0069980 A1, US 2010/0069984 A1, US 2010/0069985 A1 do not describe the specific implementation methods for coupling CCM therapy to the required sensors. Likewise, there is no discussion here of the specific coupling of on-demand CCM therapy to the sensor controls of pacemaker and ICD systems. Almost all of the sensors mentioned therein must be redeveloped and verified for use with CCM therapy. Most of the additional sensors place complex demands on the electrode and sensor design.

BRIEF SUMMARY OF THE INVENTION

The problem addressed by at least one embodiment of the invention is that of applying cardiac contractility modulation (CCM) on demand, i.e. to control it such that the therapy is activated only when an actual therapeutic need exists.

This problem is solved according to at least one embodiment of the invention by a cardiac stimulator having the following components:
  at least one stimulation unit which is connected or connectable to one or more stimulation electrodes, and is designed to deliver at least sub-threshold stimulation pulses for cardiac contraction modulation therapy,
  an impedance detection unit which is connected or connectable to one or more electrodes, and is designed to detect a voltage or current intensity that occurs as the result of a particular sub-threshold stimulation pulse, and, on the basis thereof, to determine a particular impedance value,
  an impedance evaluation unit which is designed to determine at least one value based on ventricular volume, and/or a value based on minute ventilation, and/or a value based on contraction time, and
  a control unit which is connected to the stimulation unit and the cardiac rhythm detection unit, and is designed to control a delivery of a stimulation pulse via the stimulation unit such that the cardiac stimulator can deliver sub-threshold stimulation pulses for cardiac contraction modulation therapy.

According to at least one embodiment of the invention, the control unit is connected to the impedance evaluation unit and is designed to control a delivery of sub-threshold stimulation pulses for cardiac contraction modulation therapy depending on the value based on ventricular volume, and/or the value based on minute ventilation, and/or the value based on contraction time.

The impedance evaluation unit is part of a CLS (Closed Loop Stimulation) sensor or HDS (Hemodynamic sensor) sensor, for instance, for generating a control signal for stimulation rate control on the basis of values based on ventricular volume or contraction time. Instead of a CLS sensor, it is also possible to use a minute ventilation sensor, which is formed at least in part by the impedance evaluation unit. Alternatively, another possible sensor is a combination of a CLS and minute ventilation sensor, which likewise comprises at least one impedance evaluation unit.

At least one embodiment of the invention makes use of the finding that the above-described CCM therapy corresponds to a V00 stimulation, i.e. stimulation is delivered without being regulated in terms of demand. To reduce current consumption (and possible negative effects), this highly energy-intensive therapy is only ever activated for a few hours a day.

Since the clinical data available so far have demonstrated an actual increase in contractility with this CCM therapy, it is suspected that this therapy can actually be used successfully as an option for so-called CRT non-responders.

Another potential disadvantage of uncontrolled therapy is the uncontrolled increase in contractility caused by CCM stimulation. In this case, contractility is also increased when the metabolic demand of the body does not require increased contractility. This also means there is a risk that the metabolic demand of the heart will be permanently increased due to the increase in contractility since cardiac insufficiency can be worsened further by this unspecific therapy. If this cannot always be controlled, then progressive decompensation may occur instead of the desired reverse remodeling of the myocardium.

The cardiac stimulator according to the invention can be a CLS-controlled stimulator (pacemaker or ICD/CRT-D), for instance, which is supplemented with a demand-controlled CCM therapy unit such that the CCM therapy is delivered only if it is actually required according to the cardiac state. The CCM current consumption, which has always been excessive, can therefore be lowered significantly, and possible progressive decompensation can be prevented.

In a preferred variant embodiment, the cardiac stimulator comprises a cardiac rhythm detection unit which is designed to detect an intrinsic heart rate, wherein the control unit is connected to the cardiac rhythm detection unit and is designed to determine an indicated heart rate on the basis of the ventricular volume-based value, and to prevent delivery of sub-threshold stimulation pulses for cardiac contraction modulation therapy when the heart rate indicated by the ventricular volume-based value or a change in the indicated heart rate corresponds qualitatively to an intrinsic heart rate or the change of an intrinsic heart rate. Such a cardiac stimulator makes use of the finding that increased metabolic demand in a healthy individual brings about an increase in heart rate and, associated therewith, an increase in contractility, thereby making it possible to determine, on the basis of a natural increase in heart rate, i.e. an increase in the sinus rhythm, that the increase in contractility is adequate. If this is not demonstrated after evaluation of ventricular volume-based values, then cardiac contraction modulation therapy—i.e. the delivery of related stimulation pulses during the absolute refractory period of a particular heart—can be initiated.

The following alternative sub-variants result:

Cardiac contraction modulation therapy is initiated whenever the CLS sensor specifies a heart rate increase (positive feedback).

Cardiac contraction modulation therapy is initiated whenever the CLS sensor specifies a reduction in heart rate (negative feedback).

According to a particularly preferred variant embodiment, the control unit is designed to initiate cardiac contraction modulation therapy whenever the patient's intrinsic heart rate increases, when sinus rhythm has been detected, but the increase in frequency specified by the CLS sensor lags behind the intrinsic increase in heart rate (corresponds to a diagnosed contractility deficit despite increased metabolic demand).

According to a further preferred variant embodiment, the impedance evaluation unit as well as a (further) activity sensor are provided, e.g. an accelerometer which is known per se, and which likewise delivers an output signal that indicates a patient's metabolic demand. The output signal of the accelerometer can then be processed by the control unit as a plausibility check.

Preferably, the control unit is designed to initiate cardiac contraction modulation therapy whenever the output signal of the impedance evaluation unit indicates an increase in heart rate, although the accelerometer signal does not indicate an increase in frequency.

According to a further preferred variant embodiment, a particular sub-threshold current or voltage pulse used for an impedance measurement is a stimulation pulse for contraction modulation therapy. Such a cardiac stimulator permits the use of a combination CLS and HDS sensor for controlling cardiac contractility modulation therapy (CCM), wherein the HDS sensor utilizes the CCM constant current pulses, which are present anyway, as a hemodynamic sensor system, i.e. to determine values based on ventricular volume. The preferred cardiac stimulator makes use of the fact that the bipolar constant current pulses, which are preferred for CCM therapy, basically correspond to the current pulses used in the so-called HDS sensor principle. However, the CCM current pulses have a multiple of the current intensity, and so a much better signal-to-noise ratio is expected in this case, thereby making a simpler sensor evaluation possible. The CCM current pulses are not available during the entire ventricular contraction, however, and so, in contrast to HDS, a parameter corresponding to the systolic discharge cannot be determined, although trend monitoring of the end-diastolic volume (EDV) becomes available as a control parameter for the CCM therapy. (See FIGS. 6, 7 and 8, 9).

According to the latter variant embodiment, the cardiac stimulator is a CRM stimulator (pacemaker, ICD, CRT-D) comprising
a closed loop sensor (CLS) for frequency control, and
a module for cardiac contractility modulation (CCM), and
a further impedance-sensor device that senses the image of the CCM constant-current pulses on the bipolar left-ventricular electrode and converts same to a trend parameter of the end-diastolic volume, and
comprising at least one device for coordination between the CRM stimulation and CCM therapy,
wherein the CCM therapy is always controlled depending on the CLS sensor signal.

The sensing of contractility information, i.e. the determination of the ventricular volume-based value using impedance measurement, can also be performed in the manner known per se via closed loop stimulation using a continuous intracardial impedance measurement on a ventricular electrode selectively in the right ventrical, in the left ventrical, in a bipolar manner, or a unipolar manner.

The cardiac stimulator for cardiac contractility modulation therapy is preferably simultaneously an implantable cardioverter/defibrillator (ICD), a biventricular cardiac pacemaker for cardiac resynchronization therapy (CRT-P) or a combination of a biventricular cardiac pacemaker for cardiac resynchronization therapy, and a cardioverter/defibrillator (CRT-D).

DESCRIPTION OF THE DRAWINGS

At least one embodiment of the invention is explained in greater detail with reference to embodiments and the drawings. In the drawings.

DETAILED DESCRIPTION OF THE INVENTION

Figure 1:
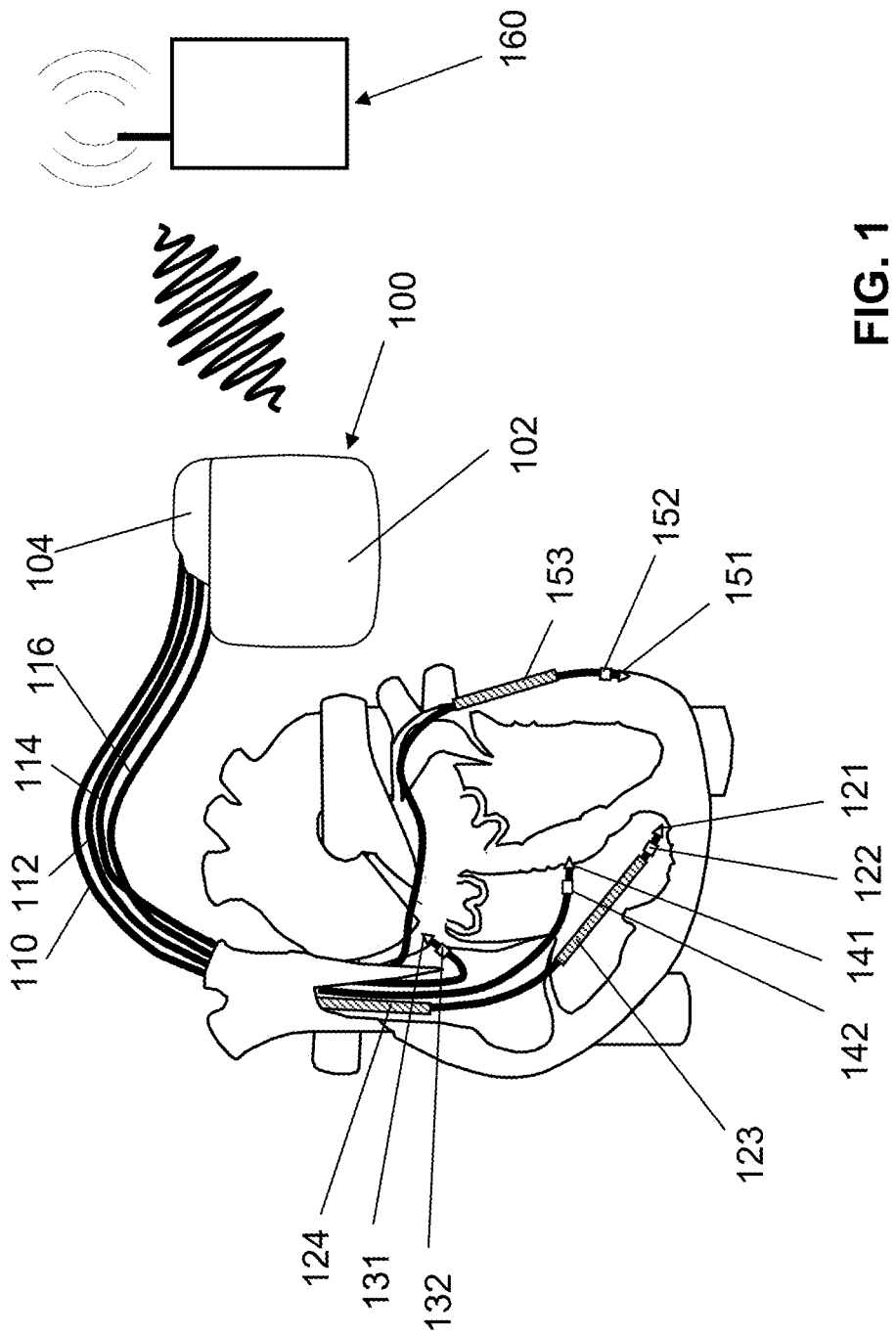
FIG. 1 shows an implantable cardiac stimulator as CCM-CRT-D

FIG. 1 shows, as an example of implementation, a three-chamber ICD system having a switchable CRT-CCM function. The cardiac stimulator (pulse generator or a simple generator) 100 is connected to a plurality of implantable electrode leads 110, 112, 114 and 116. Generator 100 comprises a housing 102 which, in this example, is composed of metal and is therefore electrically conductive, and is hermetically sealed housing 102 contains electronic and electrical components of generator 100, such as a battery, control electronics, stimulation pulse generators, sensing units comprising appropriate amplification and filter electronics. The components are detachably connected to electrode leads 110, 112, 114 and 116 via electrical plug connectors in a connector housing 104 (which is also referred to as a header).

For purposes of right-ventricular sensing and stimulation, right-ventricular electrode lead 110 comprises a right-ventricular tip electrode 121 and a right-ventricular ring electrode 122 on the distal end. The measurement pulses for the CLS sensor are delivered via right-ventricular tip electrode 121. Generator housing 100 functions as the counterelectrode in this case. A distal shock coil 123 and, optionally, a proximal shock coil 124 are installed on the electrode lead for delivery of defibrillation shocks.

Right-atrial electrode lead 116 comprises, on distal end thereof, a bipolar sensing and stimulation pole (comprising a right-atrial tip electrode 131 and a right-atrial ring electrode 132), and is used to sense the atrial rhythm and, as necessary, is used for atrial stimulation.

For CCM stimulation—i.e. cardiac contractility modulation therapy—one or more right-ventricular septal electrode leads 112 are provided, which deliver CCM pulses to the ventricular septum via a tip electrode 141 and ring electrode 142.

Optimally, the system also comprises a left-ventricular or CS (coronary sinus) electrode lead for delivery of stimulation pulses for cardiac resynchronization (CRT) via a left-ventricular tip electrode 151 and a left-ventricular ring electrode 152. A left-ventricular shock coil 153 is provided as an option to ensure more effective defibrillation/cardioversion.

Communication with external devices 160 for programming, control, and data transmission takes place via a wireless, bidirectional telemetry unit.

Cardiac stimulator 100 makes use of the following inter-relationship:

When a physiological increase in frequency occurs due to physical or mental stress, both heart rate and contractility always increase (positive inotropism). This interrelationship has been utilized so far by pacemaker systems for purposes of frequency control, by detecting the contractility dynamics of the heart using a right-ventricular, unipolar impedance measurement, and combining this information with a plausibility check by the accelerometer sensor to attain physiological closed loop frequency control in chronotropically incompetent patients (this is the principle utilized in the BIOTRONIK® CLS pacemaker). The sensor variable, which is ascertained in this manner and is derived from the impedance signal, has been demonstrated to be suitable of use in frequency control of a pacemaker, but should not be interpreted as a direct measure of hemodynamics.

For the physiological control of CCM therapy, the aforementioned CLS principle is now used, as follows: given chronotropic competence, an inotropic incompetance is detected by the CLS sensor, and CCM therapy is initiated as needed.

Preferably, CCM therapy is administered whenever the increase in frequency specified by the CLS sensor actually lags behind the actual increase in heart rate. A precondition therefor is detection of sinus rhythm. Other control algorithms based on the same fundamental principle can also be developed depending on the underlying illness and the intensity of the cardiac insufficiency.

Figure 2:
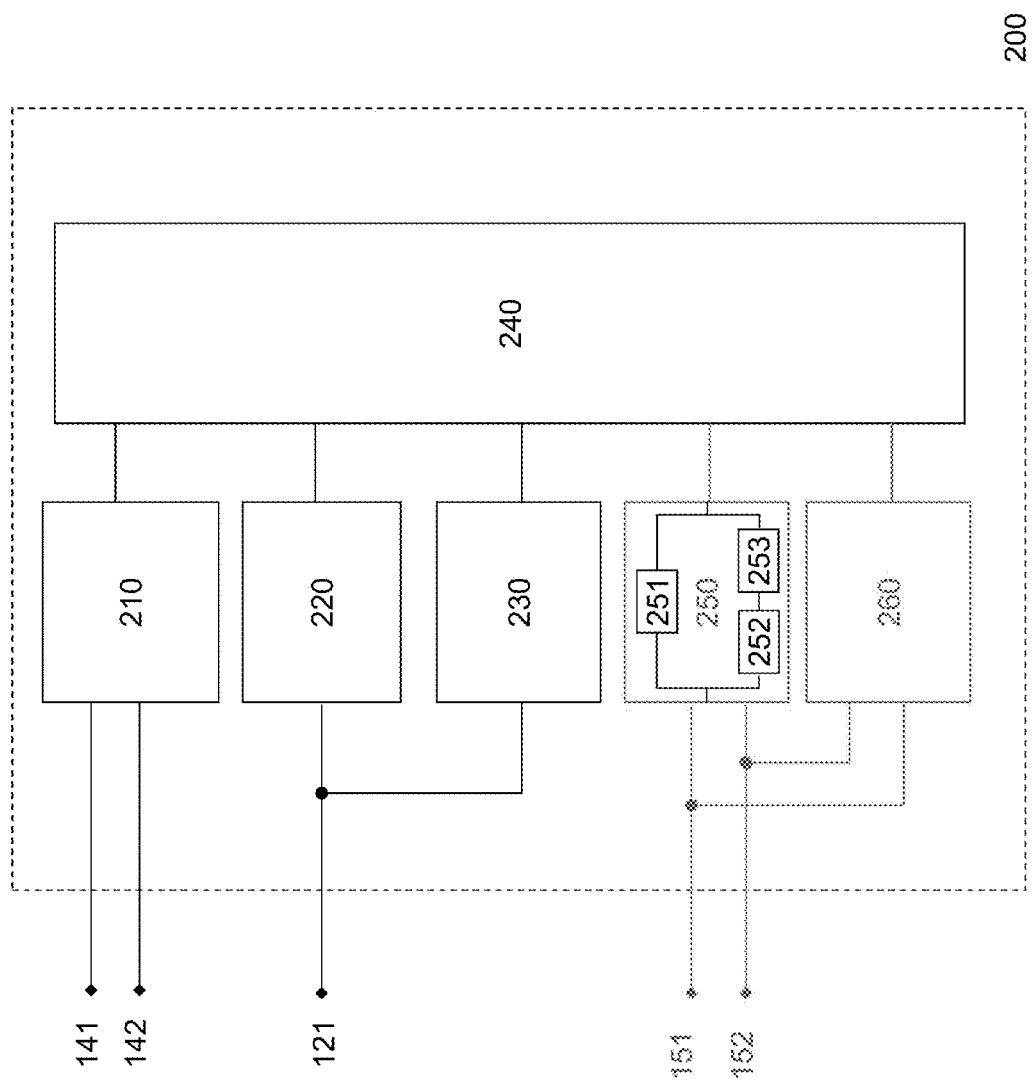
FIG. 2 shows a block diagram of a few components of the cardiac stimulator in FIG. 1.

FIG. 2 shows a schematically simplified block diagram of a simple, CLS/HDS-controlled CCM system. It comprises the following selected components, which were described with reference to FIG. 1: Generator 100, right-ventricular tip electrode 121 for unipolar impedance measurement for the CLS sensor and CCM electrode 141, 142.

CCM electrode connections 141, 142 are connected to a CCM pulse generator/synchronization unit 210, which automatically delivers the typical CCM pulses in the absolute ventricular refractory period. These pulses are likewise used as HDS measurement pulses. The CCM pulse generator is a stimulation unit.

Right-ventricular electrode connector 121 is connected to a sensing and cardiac rhythm detection unit 220 in order to determine the ventricular rate and, if applicable, the ventricular refractory period. In addition, right-ventricular electrode 121 is connected to a unipolar impedance detection unit 230 for determination of the CLS signal. Impedance detection unit 230 delivers—via right-ventricular electrode 121 and generator housing 200—constant-current pulses for determination of intracardiac impedance during a ventricular contraction. Constant-current pulses are depicted in FIG. 3.

Cardiac rhythm detection unit 220 and impedance detection unit 230 are connected to an evaluation and control unit 240. It evaluates the frequency and CLS signals such that a relationship is established between heart rate and CLS signal and, depending thereon (see FIG. 4), CCM pulse generator 210—which is likewise connected to the evaluation and control unit—is activated or deactivated.

Bipolar connectors for left-ventricular electrodes 151, 152 are connected to left-ventricular stimulation and sensing unit 250, and to impedance evaluation unit 260. This impedance evaluation unit evaluates the voltage changes generated by the CCM pulses at bipolar electrode 151, 152 such that a parameter corresponding to the end-diastolic pressure can be determined. The stimulation and sensing unit 250 also comprises appropriate amplification 251, 252 and filter 253 electronics.

Figure 3:
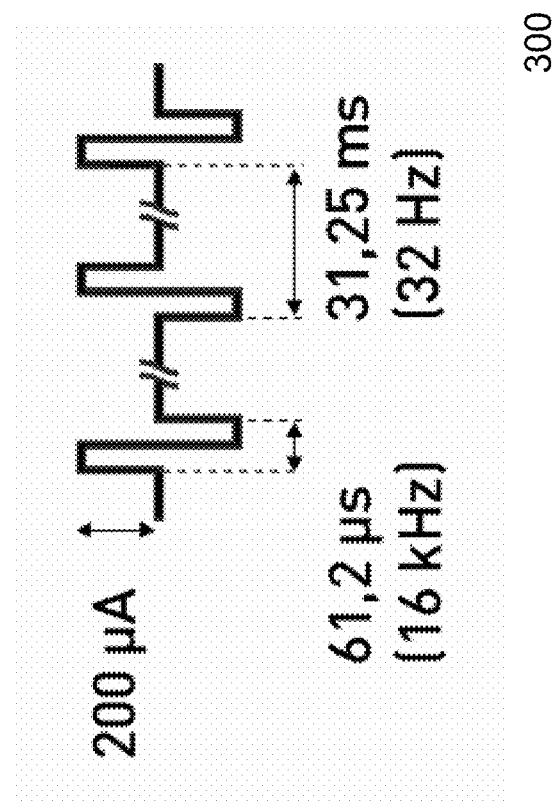
FIG. 3 shows measurement pulses for contractility measurement.

FIG. 3 shows typical current pulses 300 for continuous intracardiac impedance measurement using an impedance-based hemodynamic sensor (HDS sensor). Current pulses 300 are delivered e.g. continuously or always after a ventricular event for a certain period of time, between right-ventricular tip electrode 121 and generator housing 102. The recording of the voltage required to supply the constant current yields the CLS raw signal.

Figure 4:
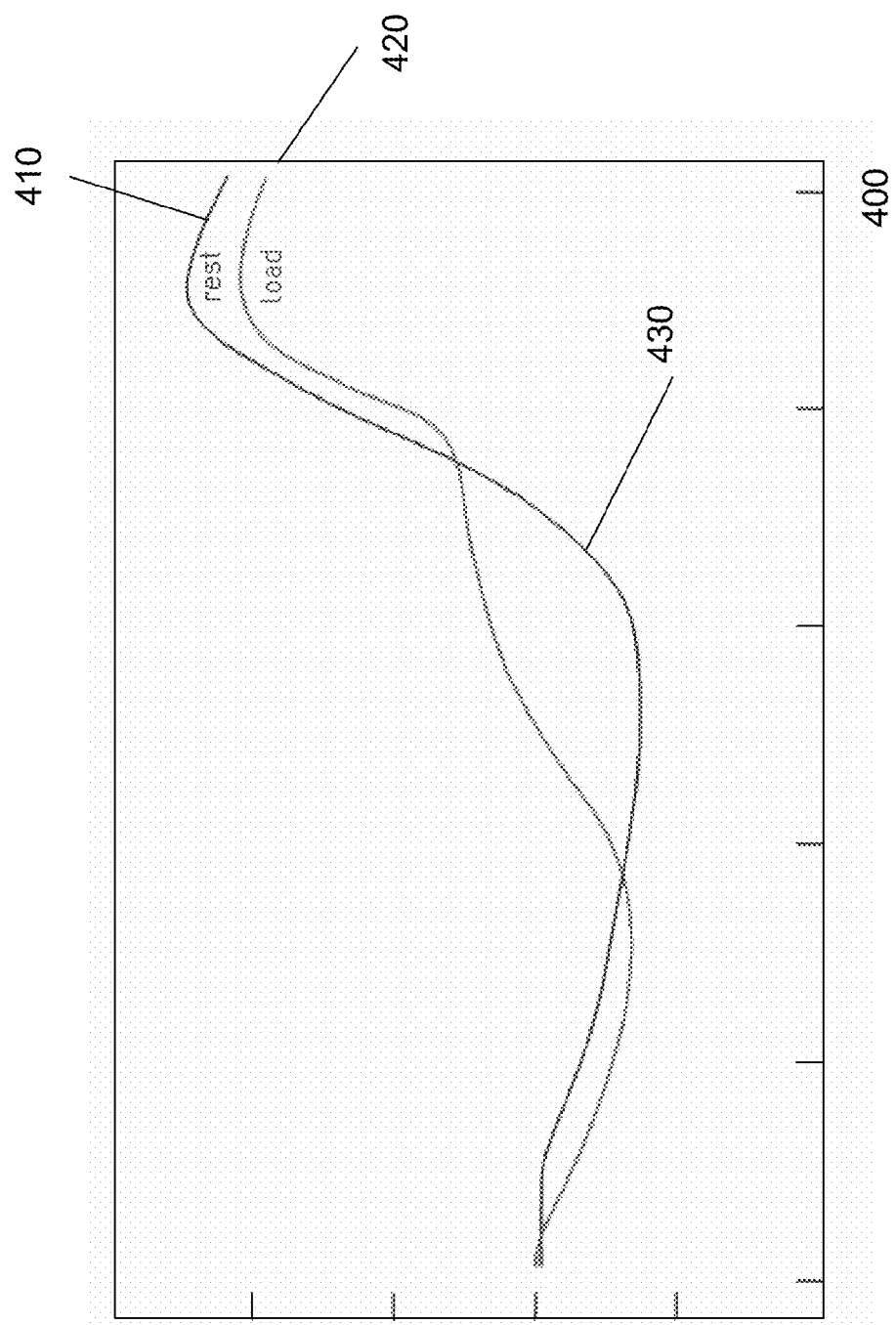
FIG. 4 shows a CLS sensor.

FIG. 4 shows a simplified depiction of the determination of the CLS sensor signal on the basis of the unipolar right-ventricular impedance signal that was measured.

In the system, a reference impedance curve 410 is recorded continuously under resting conditions (e.g. at a correspondingly lower heart rate, or the like). Said reference curve is compared continuously to a current impedance curve 420. The comparison is preferably carried out by determining the area difference 430 between the two curves. If the area difference exceeds a certain value, it can be assumed that contraction dynamics have increased.

Figure 5:
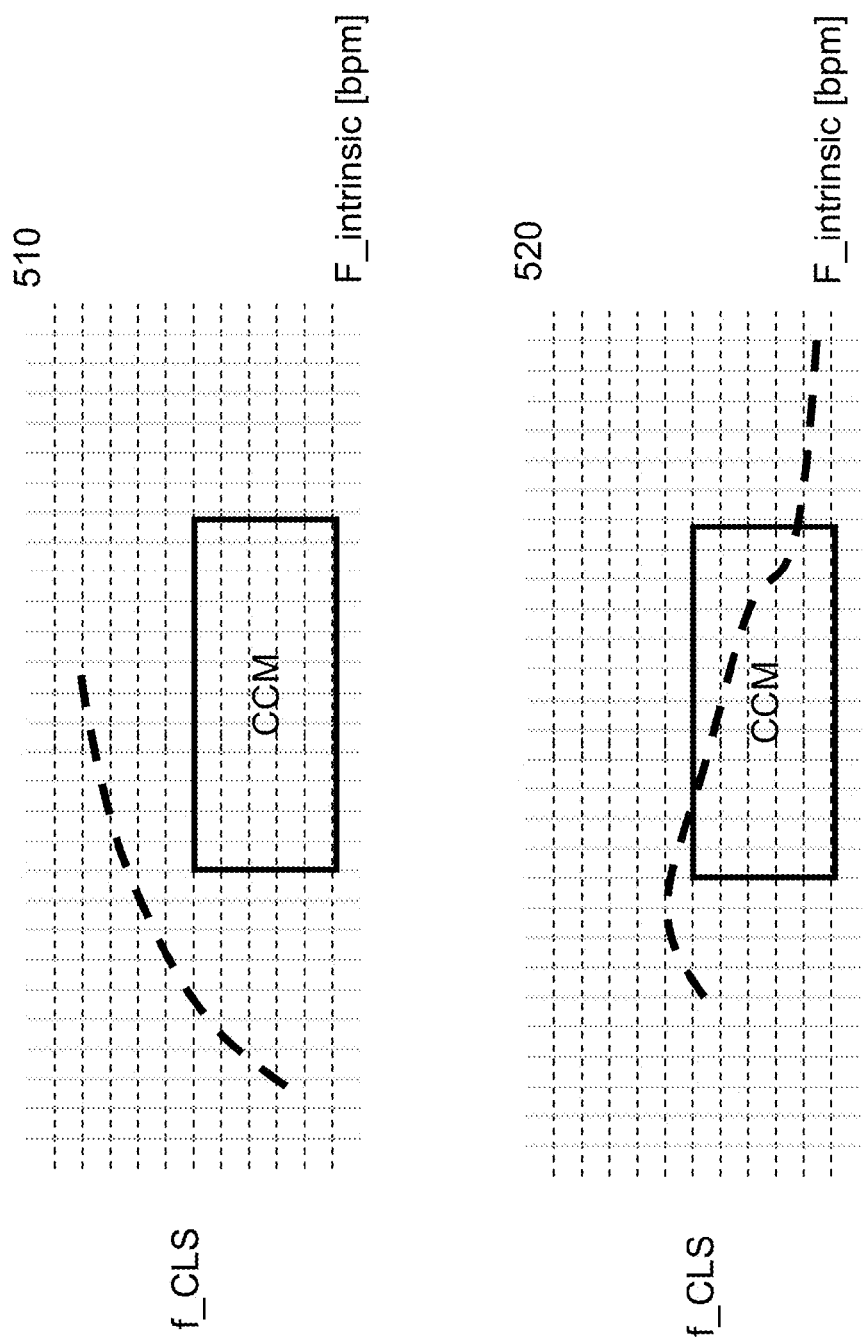
FIG. 5 shows an example of a physiological CCM activation

FIG. 5 shows one possible control of cardiac contractility modulation therapy (CCM therapy) using the system described above. If the CLS sensor signal (f_CLS) follows an intrinsic increase in heart rate (f_intrinsic) to a physiologically sufficient extent, the CLS curve remains outside of CCM therapy range 510. If this is not the case, CCM therapy is activated 520, provided the heart rate does not exceed a critical frequency.

The limits of the range within which therapy is required can be programmed in a patient-specific manner.

The fundamental principle that is shown can be supplemented with a device for detection of sinus rhythm (using atrial signals), in order to evaluate the intrinsic increase in frequency only if there is a physiological increase in frequency, and not a pathophysiological increase in frequency. A known discrimination algorithm such as BIOTRONIK® SMART™ can be used in this case, for instance.

Figure 6:
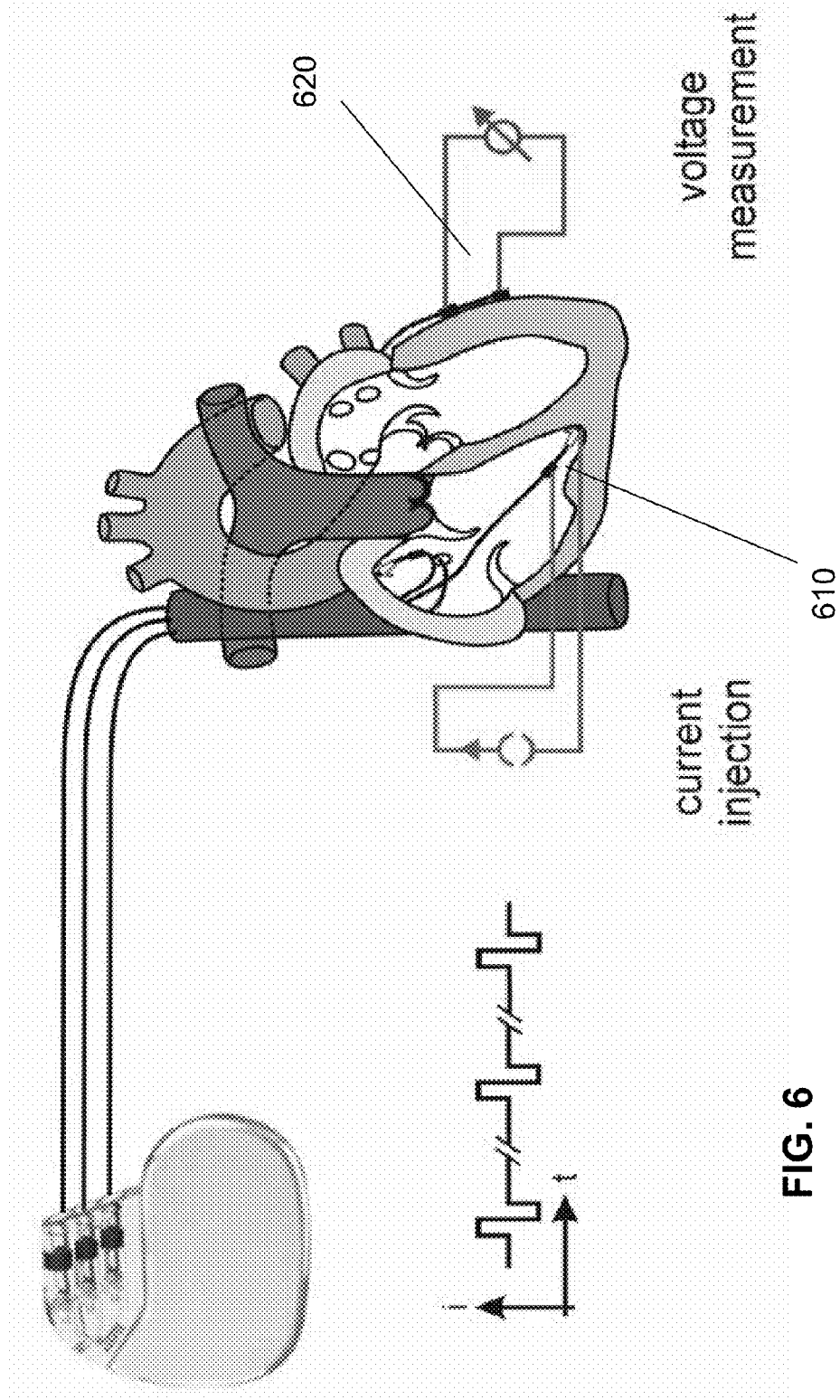
FIG. 6 shows HDS impedance measurement

FIG. 6 shows the measuring procedure known as the HDS principle for determination of the relative systolic discharge. In this case, bipolar right-ventricular electrode 610 is used to impress a constant current for the duration of the entire cardiac cycle, and the image thereof is sensed at bipolar left-ventricular electrode 620.

Figure 7:
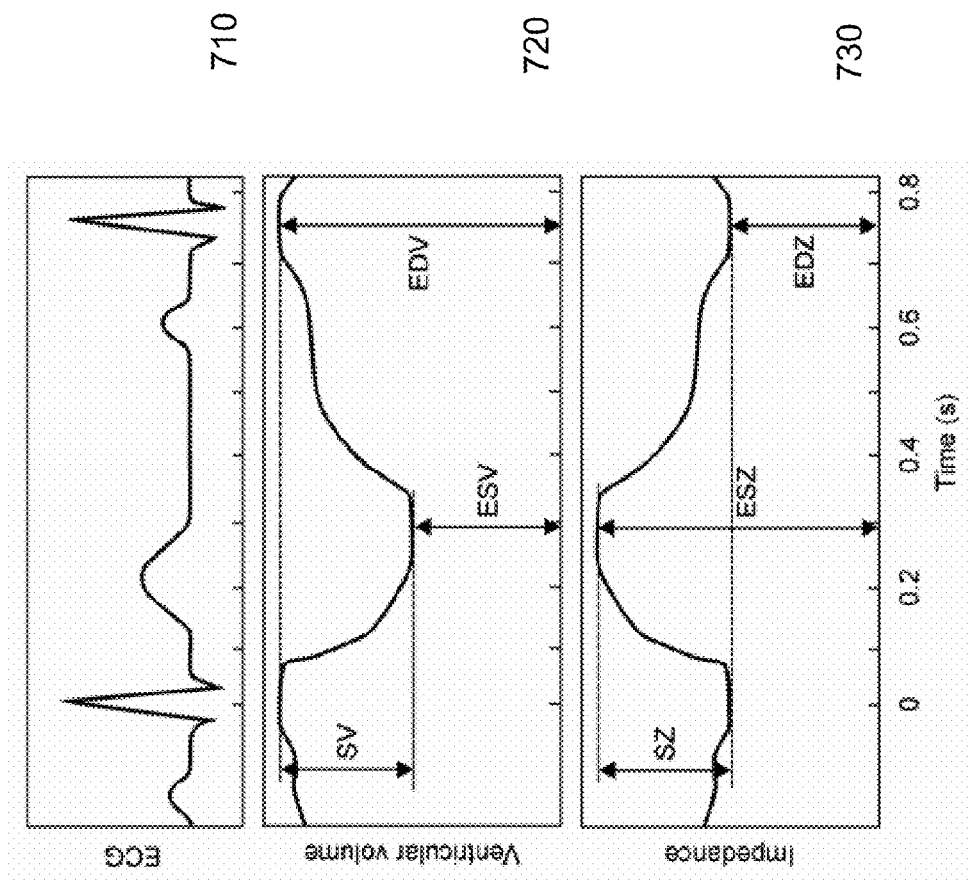
FIG. 7 shows HDS impedance measurement

FIG. 7 shows the determination of systolic discharge (SV) on the basis of HDS impedance curve 730. Superficial ECG 710 is shown in the upper channel and, below that, the plot of ventricular volume curve 720. The behavior of impedance 720 recorded per the HDS principle is inverse to that of volume curve 720, since a large ventricular blood volume is expressed as reduced impedance due to the good conductivity of blood. On the basis of the difference (SZ) between the end-diastolic impedance (EDZ) and the end-systolic impedance (ESZ), a parameter can now be obtained that correlates with the systolic discharge (SV), i.e. the relative variation in systolic discharge can therefore be recorded and used to control the implant.

Figure 8:
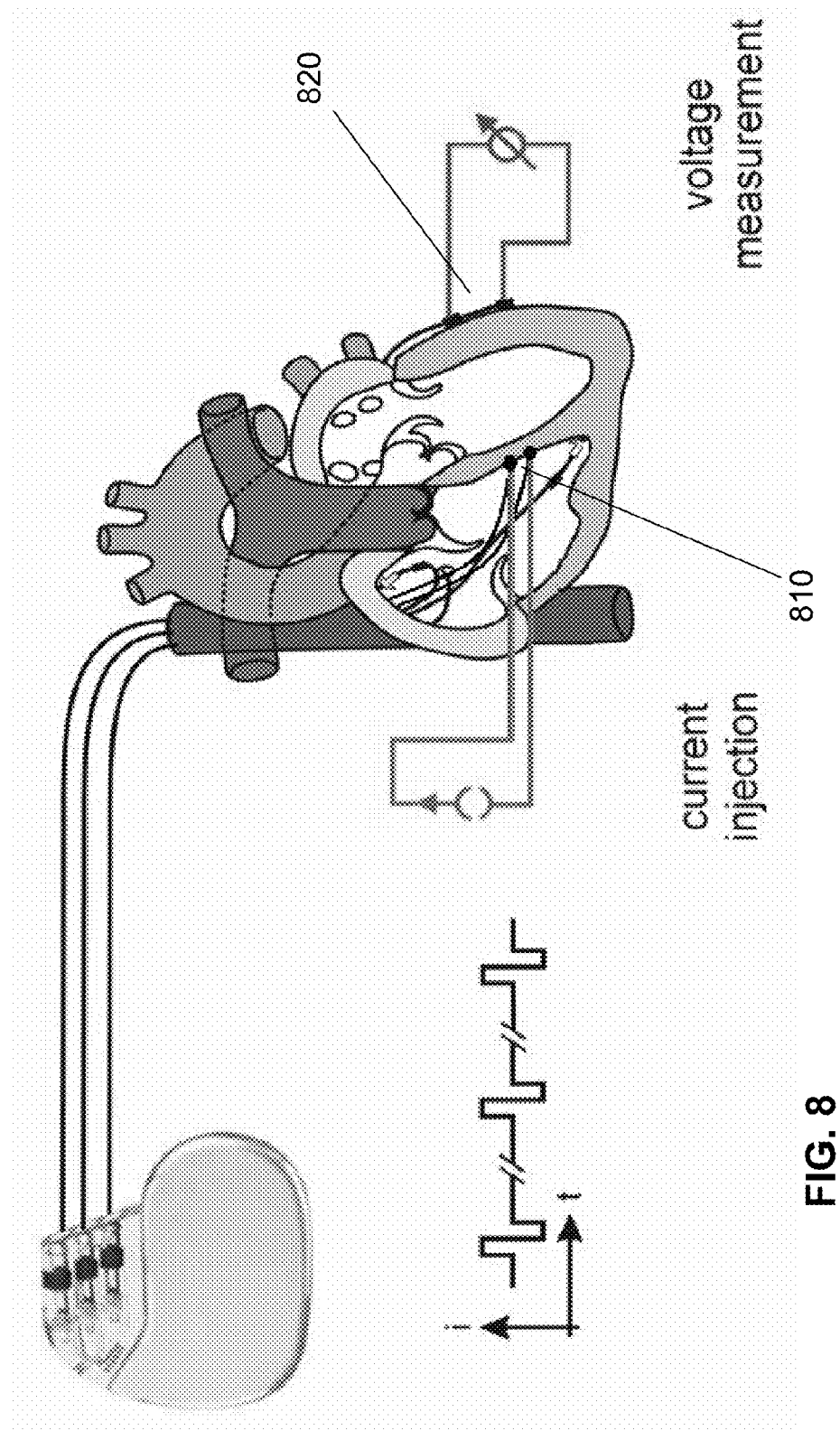
FIG. 8 shows CCM impedance measurement

FIG. 8 shows the procedure used to perform CCM impedance measurement, which is based on the HDS principle, for determination of the relative end-diastolic volume. In this case, current is supplied via bipolar septal CCM electrodes 810 in the form of CCM therapy pulses.

Bipolar left-ventricular electrode 820 is used, in turn, to sense the impedance test pulses.

Figure 9:
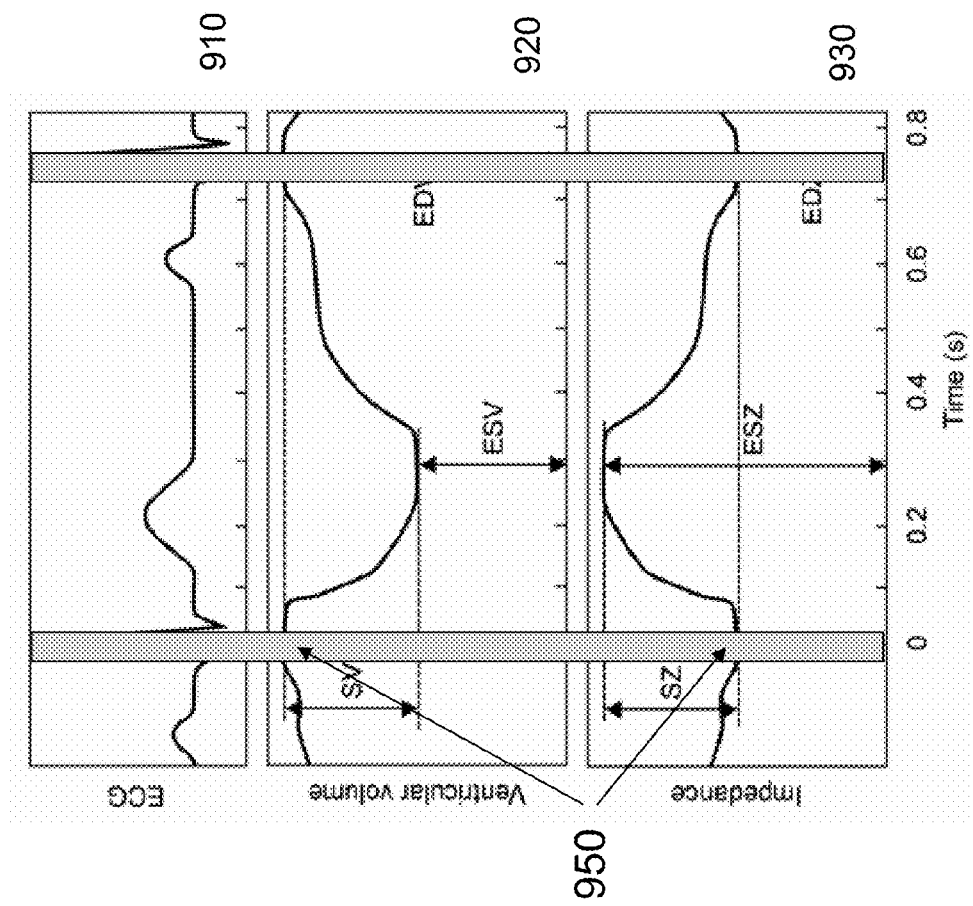
FIG. 9 shows CCM impedance measurement

FIG. 9 shows the determination of the end-diastolic volume (910: ECG, 920: ventricular volume, 930: impedance curve). The CCM pulses are much greater in terms of current amplitude than the permissible HSD measuring pulses. The CCM pulses can therefore be delivered only during the absolute refractory period and not for the entire duration of the cardiac cycle, without inducing an arrhythmia. For this reason, the impedance measurement can be carried out using the CCM pulses only in defined measurement windows 950 for a few 10 milliseconds, and so a systolic discharge parameter cannot be determined. However, the measurements carried out in the individual measurement windows can record a relative variation of the end-diastolic volume, and can therefore be used as a suitable parameter for implant control, in particular for CCM therapy as well.

Advantages of the use of CCM pulses are the expected, substantially better signal-to-noise ratios of the measurement, and the favorable position of the septal electrode for current supply.

The cardiac stimulator that is presented offers the advantage of preventing potential decompensation by permanent CCM stimulation while significantly lowering the energy required for CCM stimulation.

The solution has the decisive advantage that the CLS sensor used for physiological CCM control can already operate as a sensor for frequency adaptation.

In addition, the determination of the end-diastolic volume with CCM therapy enables the course of therapy to be monitored in an adequate manner, and can be used for implant control without the need for additional electrodes.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A cardiac stimulator comprising
at least one stimulation unit (210) which is connected or connectable to one or more stimulation electrodes, and which is configured to deliver at least sub-threshold stimulation pulses for cardiac contraction modulation therapy;
a cardiac rhythm detection unit (220);
an impedance detection unit (230) which is connected or connectable to one or more electrodes, and which is configured to detect a voltage or current intensity that occurs as the result of a particular sub-threshold stimulation pulse, and, based thereon, to determine a particular impedance value;
an impedance evaluation unit (260) which is configured to determine at least one value based on ventricular volume, and/or at least one value based on minute ventilation, and/or at least one value based on contraction time; wherein the impedance evaluation unit is further configured to determine an increase in stimulation rate;
a control unit (240) which is connected to the at least one stimulation unit, the cardiac rhythm detection unit, the impedance detection unit, and the impedance evaluation unit wherein the control unit is configured to
control a delivery of the sub-threshold stimulation pulses for the cardiac contraction modulation therapy that depend on the at least one value based on ventricular volume, and/or the at least one value based on minute ventilation, and/or the at least one value based on contraction time;
wherein the control unit is configured to initiate the cardiac contraction modulation therapy whenever the impedance evaluation unit determines an increase in heart rate; and
wherein the control unit is configured to initiate the cardiac contraction modulation therapy whenever the an increase in heart rate is determined, when sinus rhythm has been detected, and when an increase in stimulation rate determined by the impedance evaluation unit lags behind the increase in heart rate.

2. The cardiac stimulator according to claim 1, wherein said voltage or current intensity used for an impedance measurement is said sub-threshold stimulation pulse for the contraction modulation therapy.

3. The cardiac stimulator according to claim 1, wherein the cardiac rhythm detection unit is configured to detect an intrinsic heart rate, wherein the control unit is configured to determine an indicated heart rate based on the ventricular volume, and to prevent delivery of the sub-threshold stimulation pulses for the cardiac contraction modulation therapy when the indicated heart rate based on the ventricular volume or a change in the indicated heart rate corresponds qualitatively to the intrinsic heart rate or the change of the intrinsic heart rate.

4. The cardiac stimulator according to claim 1, wherein the impedance evaluation unit is part of a Closed Loop Stimulation (CLS) sensor or a Hemodynamic Sensor (HDS) that is configured to generate a control signal for stimulation rate control based on the ventricular volume.

5. The cardiac stimulator to claim 1, wherein the impedance evaluation unit is part of a combination of a Closed Loop Stimulation (CLS) sensor and a minute ventilation sensor.

6. The cardiac stimulator according to claim 1, wherein the control unit is configured to initiate the cardiac contraction modulation therapy whenever the impedance evaluation unit determines a reduction in heart rate.

7. The cardiac stimulator according to claim 1, further comprising an activity sensor configured to deliver an output signal indicative of metabolic demand.

8. The cardiac stimulator according to claim 7, wherein the control unit is configured to process the output signal of the activity sensor as a plausibility check.

9. The cardiac stimulator according to claim 7, wherein the control unit is configured to initiate the cardiac contraction modulation therapy whenever the impedance evaluation unit indicates an increase in heart rate, and the output signal of the activity sensor does not indicate the increase in heart rate.

10. The cardiac stimulator according to claim 8, wherein the control unit is configured to initiate the cardiac contraction modulation therapy whenever the impedance evaluation unit indicates an increase in heart rate, and the output signal of the activity sensor does not indicate the increase in heart rate.

11. The cardiac stimulator according to claim 1, wherein the cardiac stimulator is configured to determine ventricular volume based on impedance measurement via continuous intracardial impedance measurement at a ventricular electrode.

12. The cardiac stimulator according to claim 1, wherein the cardiac stimulator is a cardiac stimulator for the cardiac contractility modulation therapy and, simultaneously, an implantable cardioverter/defibrillator (ICD), a biventricular cardiac pacemaker for cardiac resynchronization therapy (CRT-P) or a combination of a biventricular cardiac pacemaker for cardiac resynchronization therapy and a cardioverter/defibrillator (CRT-D).

13. A cardiac stimulator comprising
at least one stimulation unit (210) which is connected or connectable to one or more stimulation electrodes, and which is configured to deliver at least sub-threshold stimulation pulses for cardiac contraction modulation therapy;
a cardiac rhythm detection unit (220);
an impedance detection unit (230) which is connected or connectable to one or more electrodes, and which is configured to detect a voltage or current intensity that occurs as the result of a particular sub-threshold stimulation pulse, and, based thereon, to determine a particular impedance value;
an impedance evaluation unit (260) which is configured to determine at least one value based on ventricular volume, and/or at least one value based on minute ventilation, and/or at least one value based on contraction time; wherein the impedance evaluation unit is further configured to determine an increase in stimulation rate;
a control unit (240) which is connected to the at least one stimulation unit, the cardiac rhythm detection unit, the impedance detection unit, and the impedance evaluation unit wherein the control unit is configured to
control a delivery of the sub-threshold stimulation pulses for the cardiac contraction modulation therapy that depend on the at least one value based on ventricular volume, and/or the at least one value based on minute ventilation, and/or the at least one value based on contraction time;
wherein the control unit is configured to initiate the cardiac contraction modulation therapy whenever the impedance evaluation unit determines an increase in heart rate; and
wherein the control unit is configured to initiate the cardiac contraction modulation therapy whenever the an increase in heart rate is determined, when sinus rhythm has been detected, and when an increase in stimulation rate determined by the impedance evaluation unit lags behind the increase in heart rate; and
an activity sensor configured to deliver an output signal indicative of metabolic demand;
wherein the control unit is configured to initiate the cardiac contraction modulation therapy whenever the impedance evaluation unit indicates an increase in heart rate, and the output signal of the activity sensor does not indicate the increase in heart rate.

* * * * *